United States Patent
Murphy et al.

(10) Patent No.: US 11,370,998 B2
(45) Date of Patent: Jun. 28, 2022

(54) SYNERGISTIC CELLULASE-SURFACTANT INTERACTIONS FOR DEGRADATION OF BACTERIAL CELLULOSE

(71) Applicant: Ecolab USA Inc., Saint Paul, MN (US)

(72) Inventors: Jesse Murphy, Saint Paul, MN (US); Lyndal Jensen, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 235 days.

(21) Appl. No.: 16/441,413

(22) Filed: Jun. 14, 2019

(65) Prior Publication Data

US 2019/0382689 A1    Dec. 19, 2019

Related U.S. Application Data

(60) Provisional application No. 62/684,984, filed on Jun. 14, 2018.

(51) Int. Cl.
| | | |
|---|---|---|
| C11D 3/386 | (2006.01) | |
| C11D 1/722 | (2006.01) | |
| C11D 3/37 | (2006.01) | |
| C11D 3/20 | (2006.01) | |

(52) U.S. Cl.
CPC .......... *C11D 3/38654* (2013.01); *C11D 1/722* (2013.01); *C11D 3/2065* (2013.01); *C11D 3/2086* (2013.01); *C11D 3/3707* (2013.01)

(58) Field of Classification Search
CPC ... C11D 3/38654; C11D 1/722; C11D 3/2065; C11D 3/2086; C11D 3/3707; C11D 3/38645; C12N 9/2437
See application file for complete search history.

(56) References Cited

U.S. PATENT DOCUMENTS

| | | |
|---|---|---|
| 4,320,147 A | 3/1982 | Schaeufele |
| 5,389,685 A | 2/1995 | Smith et al. |
| 5,545,749 A | 8/1996 | Smith et al. |
| 5,547,990 A | 8/1996 | Hall et al. |
| 5,721,205 A | 2/1998 | Barnabas et al. |
| 5,783,537 A | 7/1998 | Ahmed et al. |
| 5,833,741 A | 11/1998 | Walker |
| 5,939,369 A | 8/1999 | Chowhan et al. |
| 5,975,095 A | 11/1999 | Ahmed et al. |
| 6,020,293 A | 2/2000 | Ahmed et al. |
| 6,376,451 B1 | 4/2002 | Teasdale et al. |
| 6,464,764 B1 | 10/2002 | Lichtenberg et al. |
| 6,583,181 B1 | 6/2003 | Chiang et al. |
| 6,855,531 B2 | 2/2005 | Shulein et al. |
| 6,939,840 B2 | 9/2005 | Lichtenberg et al. |
| 7,186,675 B2 | 3/2007 | Meine et al. |
| 7,553,806 B2 | 6/2009 | Man et al. |
| 8,221,733 B2 | 7/2012 | Lichtenberg et al. |
| 8,992,632 B2 | 3/2015 | Holzhauer et al. |
| 9,282,746 B2 | 3/2016 | Amin et al. |
| 9,738,857 B2 | 8/2017 | Ortmann et al. |
| 10,183,087 B2 | 1/2019 | Franciskovich et al. |
| 10,206,392 B2 | 2/2019 | Kloeppel et al. |
| 10,285,400 B2 | 5/2019 | Lei et al. |
| 2003/0029812 A1 | 2/2003 | Burns et al. |
| 2003/0114342 A1 | 6/2003 | Hall |
| 2003/0187073 A1 | 10/2003 | Lichtenberg et al. |
| 2004/0220275 A1 | 11/2004 | Lutzeler et al. |
| 2005/0079594 A1 | 4/2005 | Marion |
| 2005/0124723 A1 | 6/2005 | Fritschi et al. |
| 2006/0293212 A1 | 12/2006 | Griese et al. |
| 2012/0213759 A1 | 8/2012 | Karsten et al. |
| 2013/0130358 A1 | 5/2013 | Davanzo |
| 2013/0203644 A1 | 8/2013 | Lant et al. |
| 2013/0303430 A1 | 11/2013 | Reinoso Garcia et al. |
| 2014/0171512 A1 | 6/2014 | Kloeppel et al. |
| 2014/0274973 A1 | 9/2014 | Pedersen et al. |
| 2014/0290694 A1 | 10/2014 | Uchiyama et al. |
| 2017/0284605 A1 | 10/2017 | Janak et al. |
| 2017/0321160 A1 | 11/2017 | Lant et al. |
| 2018/0171316 A1 | 6/2018 | Spodsberg et al. |
| 2018/0179508 A1 | 6/2018 | Spodsberg et al. |

(Continued)

FOREIGN PATENT DOCUMENTS

| | | |
|---|---|---|
| EP | 0551413 B1 | 7/1993 |
| EP | 0593662 B1 | 4/1994 |

(Continued)

OTHER PUBLICATIONS

Dow catalog, 2006, Nonionic Surfactants, TERGITOL™ 15-S Surfactants, p. 1-12, retrieved from dow.com on Aug. 29, 2021. (Year: 2006).*
Hsieh et al., "Cellobiohydrolase and endoglucanase respond differently to surfactants during the hydrolysis of cellulose". Biotechnology for Biofuels, vol. 8:52, 10 pages, 2015.
Mizutani et al., "Effect of a nonionic surfactant on Trichoderma cellulase treatments of regenerated cellulose and cotton yarns", Cellulose, vol. 9, pp. 83-89, 2002.
Ecolab USA Inc, in connections with PCT/US2019/037158 filed Jun. 14, 2019, "The International Search Report and the Written Opinion of the International Searching Authority, or the Declaration", 15 pages, dated Oct. 7, 2019.
Araujo et al., "Combination of selected enzymes with cetyltrimethylammonium bromide in biofilm inactivation, removal and regrowth", Food Research International, 36 pages, Feb. 26, 2017.

(Continued)

*Primary Examiner* — Kade Ariani
(74) *Attorney, Agent, or Firm* — McKee, Voorhees & Sease, PLC

(57) ABSTRACT

The disclosure is directed to cleaning compositions, methods of making the cleaning compositions, and methods of using the cleaning compositions. The cleaning compositions comprise an enzyme composition and a nonionic surfactant having an HLB between 10 and 22. Preferably, the enzyme compositions included in the cleaning compositions comprise a cellulase, an AA9 polypeptide having cellulolytic enhancing activity, a hemicellulase, an esterase, an expansin, a laccase, a ligninolytic enzyme, a pectinase, a peroxidase, a protease, a swollenin, or a combination or mixture thereof. The compositions are useful for degradation of bacterial cellulose.

16 Claims, 4 Drawing Sheets

(56) References Cited

U.S. PATENT DOCUMENTS

| | | | |
|---|---|---|---|
| 2018/0216040 A1 | 8/2018 | Baltsen et al. | |
| 2018/0355337 A1 | 12/2018 | Spodsberg et al. | |
| 2020/0229435 A1 | 7/2020 | Malet et al. | |
| 2020/0305437 A1 | 10/2020 | McGeechan et al. | |

FOREIGN PATENT DOCUMENTS

| | | | | |
|---|---|---|---|---|
| EP | 0679714 A2 | * | 11/1995 | ......... C11D 3/38645 |
| EP | 0888434 B1 | | 1/1999 | |
| EP | 3088506 B1 | | 11/2016 | |
| EP | 3173467 A1 | | 5/2017 | |
| WO | 9732960 A1 | | 9/1997 | |
| WO | 0035283 A1 | | 6/2000 | |
| WO | 0059696 A2 | | 10/2000 | |
| WO | WO 2005/080540 A1 | * | 9/2005 | |
| WO | 2008049616 A1 | | 5/2008 | |
| WO | 2017021515 A1 | | 2/2017 | |
| WO | 2017021516 A1 | | 2/2017 | |
| WO | 2017192417 A1 | | 11/2017 | |
| WO | 2018185181 A1 | | 10/2018 | |

OTHER PUBLICATIONS

Eriksson et al., "Mechanism of surfactant effect in enzymatic hydrolysis of lignocellulose", Enzyme and Microbial Technology, vol. 31, pp. 353-364, Apr. 14, 2002.
Jurado et al., "Hard-surface cleaning using lipases: Enzyme-surfactant interactions and washing tests", J Surfact Deterg, vol. 10, pp. 61-70, Mar. 2007.

* cited by examiner

| [Stabilizer] (%) | Glycerol | PEG 200 | Sucrose | Propylene Glycol | Glucose | Dipropylene Glycol | Propylene Diol | PEG 400 | PEG 1450 |
|---|---|---|---|---|---|---|---|---|---|
| 0 | 100 | 100 | 100 | 100 | 100 | 100 | 100 | 100 | 100 |
| 5 | 84.7 | 88 | 108.9 | 85.1 | 77.9 | 71.8 | 86.8 | 85.5 | 93.8 |
| 10 | 76 | 97 | 88.6 | 45.4 | 60.2 | 55.2 | 63.9 | 71.3 | 77.4 |
| 15 | 75.3 | 104 | 63.3 | 46.5 | 29.1 | NA | NA | 70.4 | 70.7 |
| 20 | 77 | 95 | 43.8 | 32 | 27.1 | NA | NA | 38.6 | NA |

*FIG. 5*

SYNERGISTIC CELLULASE-SURFACTANT INTERACTIONS FOR DEGRADATION OF BACTERIAL CELLULOSE

CROSS-REFERENCE TO RELATED APPLICATIONS

This application claims priority under 35 U.S.C. § 119 to provisional application Ser. No. 62/684,984, filed Jun. 14, 2018, herein incorporated by reference in its entirety.

FIELD OF THE INVENTION

The present disclosure relates to compositions comprising enzyme composition and a nonionic surfactant having an HLB between 10 and 22, and methods of making and using the same. In particular, the compositions are useful for degradation of bacterial cellulose.

BACKGROUND

Bacterial cellulose and other cellulose-based deposits can be difficult to remove. It is a common problem in drains associated with food and beverage services, particularly in beverage tower drains where various sweeteners and other beverage components drain. Bacterial cellulose can form polymeric clogs, often referred to as sugar snakes. A survey in 2014 found that nearly one third of beverage tower operators had beverage tower drains with frequent clogs. This necessitates additional maintenance. Additionally, such clogs often result in malodor and attract insects such as flies. Bacterial cellulose can also be a component in slimes and biofilms. These can be difficult to remove as they often contain carbohydrates, proteins, and bacteria within a polymeric matrix having many layers. Those layers can be difficult to penetrate for full cleaning effect. Treatments for bacterial cellulose and slimes may often require additional manual cleaning steps for full effectiveness, further the enzymes employed to breakdown the sugar snakes, and in particular, the cellulose, often lose efficacy.

Accordingly, it is an objective of the present disclosure to develop compositions for cleaning bacterial cellulose deposits.

A further object of the present disclosure is to describe compositions that can retard the growth of bacterial cellulose deposits.

Still another object of the present disclosure is to provide to describe compositions having less than about 0.5 wt. % active protein concentration while maintaining cleaning efficacy.

Yet another object of the present disclosure is to describe compositions useful for treating, and methods of treating, bacterial cellulose that do not require personal protective equipment (PPE).

Other objects, advantages and features of the compositions and methods of making and using the same will become apparent from the following specification taken in conjunction with the accompanying figures.

BRIEF SUMMARY OF PREFERRED EMBODIMENTS

The present disclosure describes compositions for and methods of removing bacterial cellulose deposits, as well as methods of preparing the compositions. It is an advantage of the compositions that they do not require PPE. Still a further advantage of the compositions is that they have a synergistic reaction between the enzyme composition and surfactants that provides surprising efficacy against bacterial cellulose deposits.

In a preferred embodiment a composition for cleaning bacterial cellulose deposits comprises from about 0.01 wt. % to about 2 wt. % of an enzyme composition, from about 0.001 wt. % to about 7 wt. % of a nonionic surfactant, from about 55 wt. % to about 97 wt. % of water. Preferably, the composition has a pH of less than about 5. Preferably the enzyme composition comprises a cellulase, an AA9 polypeptide having cellulolytic enhancing activity, a hemicellulase, an esterase, an expansin, a laccase, a ligninolytic enzyme, a pectinase, a peroxidase, a protease, a swollenin, or a combination or mixture thereof.

Preferably, the nonionic surfactant has an HLB value between 10 and 22.

In a preferred embodiment a multi-part system for cleaning bacterial cellulose deposits, the cleaning composition comprises from about 0.01 wt. % to about 2 wt. % of an enzyme composition, from about 0.001 wt. % to about 7 wt. % of a nonionic surfactant, from about 55 wt. % to about 97 wt. % of water. Preferably, the composition has a pH between about 2 and about 11. Preferably the enzyme composition comprises a cellulase, an AA9 polypeptide having cellulolytic enhancing activity, a hemicellulase, an esterase, an expansin, a laccase, a ligninolytic enzyme, a pectinase, a peroxidase, a protease, a swollenin, or a combination or mixture thereof. Preferably, the nonionic surfactant has an HLB value between 10 and 22.

In a preferred embodiment a composition for cleaning bacterial cellulose deposits comprises from about 0.01 wt. % to about 2 wt. % of an enzyme, from about 0.001 wt. % to about 7 wt. % of a nonionic surfactant, from about 0.1 wt. % to about 5 wt. % of a buffering agent, and from about 55 wt. % to about 97 wt. % of water. Preferably, the composition has a pH of between about 3 and about 5. Preferably the enzyme composition comprises a cellulase, an AA9 polypeptide having cellulolytic enhancing activity, a hemicellulase, an esterase, an expansin, a laccase, a ligninolytic enzyme, a pectinase, a peroxidase, a protease, a swollenin, or a combination or mixture thereof. Preferably, the nonionic surfactant is a polyethylene glycol sorbitan ester, polyethylene glycol ether, polyoxyethylene ether, a poly(propylene glycol)-block-poly(ethylene glycol)-block-poly(propylene glycol), or mixture thereof, and has an HLB value between 10 and 22. Preferably the buffering agent comprises CAPS, CHES, HEPBS, HEPES, HEPPS, MOPS, MES, Tris, an organic acid or salt thereof, an inorganic acid or salt thereof, or a mixture thereof.

In a preferred embodiment, a cleaning composition is used to clean a bacterial cellulose deposit according to a method comprising contacting a hard surface with a cleaning composition for a sufficient time to at least partially degrade the bacterial cellulose deposit. Preferably the cleaning composition comprises from about 0.01 wt. % to about 2 wt. % of an enzyme composition, from about 0.001 wt. % to about 7 wt. % of a nonionic surfactant, from about 55 wt. % to about 97 wt. % of water; has a pH of less than about 5; wherein the enzyme composition comprises a cellulase, an AA9 polypeptide having cellulolytic enhancing activity, a hemicellulase, an esterase, an expansin, a laccase, a ligninolytic enzyme, a pectinase, a peroxidase, a protease, a swollenin, or a combination or mixture thereof; and wherein the nonionic surfactant has an HLB value between 10 and 22. Preferably, the contact time is at least about 5 seconds.

In a preferred embodiment, the hard surface is a drain, a floor, a sink, a beverage tower fluid line, or combination thereof.

While multiple embodiments are disclosed, still other embodiments may become apparent to those skilled in the art from the following detailed description, which shows and describes illustrative embodiments. Accordingly, the figures and detailed description are to be regarded as illustrative in nature and not restrictive.

BRIEF DESCRIPTION OF THE FIGURES

FIG. 5 is a table from Example 6 comparing percent degradation of a sugar snake based on varying stabilizers and stabilizer concentrations.

Figure 1:
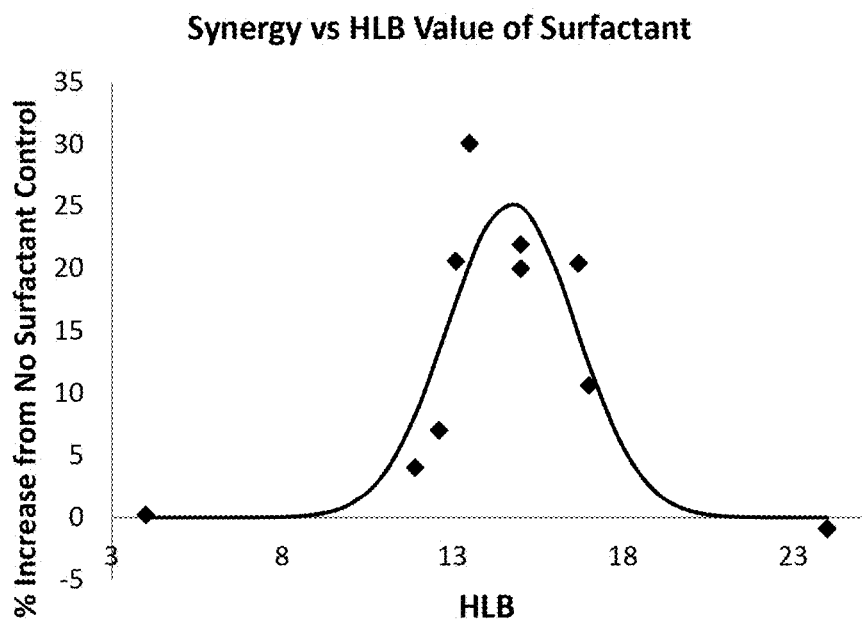
FIG. 1 is a scatter plot with a trend line from the testing in Example 1 comparing the percent degradation of a sugar snake based on increasing HLB of the surfactant.

Various embodiments of the exemplary cleaning compositions and methods of using the cleaning compositions are represented in the figures. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The present disclosure relates to compositions comprising an enzyme composition and a nonionic surfactant having an HLB value between 10 and 22. These compositions are useful for cleaning of bacterial cellulose deposits and such methods are described herein. The compositions have many advantages over existing bacterial cellulose treatment compositions. For example, an advantage of the compositions is that they provide improved removal of bacterial cellulose deposits. It is a further advantage that the compositions do not require PPE. Yet another advantage of the compositions is that they have a synergistic reaction between the enzyme composition and surfactants that provides surprising efficacy against bacterial cellulose deposits. Still a further advantage is that the compositions to preferably comprise less than about 0.5 wt. % active protein concentration, more preferably less than about 0.1 wt. % active protein concentration, while maintaining cleaning efficacy.

The embodiments described herein are not limited to particular bacterial cellulose deposits, which can vary in makeup and in location. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of the compositions and methods are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range.

References to elements herein are intended to encompass any or all of their oxidative states and isotopes.

Definitions

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

The term "about," as used herein, refers to variation in the numerical quantity that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The term "about" also encompasses amounts that differ due to different equilibrium conditions for a composition resulting from a particular initial mixture. The term "about" also encompasses these variations. Whether or not modified by the term "about," the claims include equivalents to the quantities.

As used herein, the term "oligomer" refers to a molecular complex comprised of between one and ten monomeric units. For example, dimers, trimers, and tetramers, are considered oligomers. Furthermore, unless otherwise specifically limited, the term "oligomer" shall include all possible isomeric configurations of the molecule, including, but are not limited to isotactic, syndiotactic and random symmetries, and combinations thereof. Furthermore, unless otherwise specifically limited, the term "oligomer" shall include all possible geometrical configurations of the molecule.

As used herein the term "polymer" refers to a molecular complex comprised of more than ten monomeric units and generally includes, but is not limited to, homopolymers, copolymers, such as for example, block, graft, random and alternating copolymers, terpolymers, and higher "x"mers, further including their analogs, derivatives, combinations, and blends thereof. Furthermore, unless otherwise specifically limited, the term "polymer" shall include all possible isomeric configurations of the molecule, including, but are not limited to isotactic, syndiotactic and random symmetries, and combinations thereof. Furthermore, unless otherwise specifically limited, the term "polymer" shall include all possible geometrical configurations of the molecule.

The methods and compositions of the present disclosure may comprise, consist essentially of, or consist of the components and ingredients of the present disclosure as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

The term "actives" or "percent actives" or "percent by weight actives" or "actives concentration" are used interchangeably herein and refers to the concentration of those ingredients involved in cleaning expressed as a percentage minus inert ingredients such as water or salts. It is also sometimes indicated by a percentage in parentheses, for example, "chemical (10%)."

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The term "weight percent," "wt. %," "wt. %," "percent by weight," "% by weight," and variations thereof, as used herein, refer to the concentration of a substance as the weight of that substance divided by the total weight of the composition and multiplied by 100.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is affected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the term "malodor," is synonymous with phrases like "objectionable odor" and "offensive odor," which refer to a sharp, pungent, or acrid odor or atmospheric environment from which a typical person withdraws if they are able to. Hedonic tone provides a measure of the degree to which an odor is pleasant or unpleasant. A "malodor" has a hedonic tone rating it as unpleasant as or more unpleasant than a solution of 5 wt. % acetic acid, propionic acid, butyric acid, or mixtures thereof.

For the purpose of this patent application, successful microbial reduction is achieved when the microbial populations are reduced by at least about 50%, or by significantly more than is achieved by a wash with water. Larger reductions in microbial population provide greater levels of protection.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition As used herein, the term "substantially free" refers to compositions completely lacking the component or having such a small amount of the component that the component does not affect the performance of the composition. The component may be present as an impurity or as a contaminant and shall be less than 0.5 wt. %. In another embodiment, the amount of the component is less than 0.1 wt. % and in yet another embodiment, the amount of component is less than 0.01 wt. %.

The terms "water soluble" and "water dispersible" as used herein, means that the polymer is soluble or dispersible in water in the inventive compositions. In general, the polymer should be soluble or dispersible at 25° C. at a concentration of 0.0001% by weight of the water solution and/or water carrier, preferably at 0.001%, more preferably at 0.01% and most preferably at 0.1%.

The term "weight percent," "wt. %," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt. %," etc.

The methods, systems, apparatuses, and compositions of the present disclosure may comprise, consist essentially of, or consist of the components and ingredients of the present disclosure as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

Compositions

Preferably, the compositions comprise an enzyme composition, a nonionic surfactant having an HLB value between 10 and 22, and water. In a preferred embodiment, the compositions further comprise a pH modifier and/or stabilizing agent. In a more preferred embodiment, the compositions comprise an enzyme composition, a nonionic surfactant having an HLB value between about 13 and about 18, a pH modifier and/or stabilizing agent, and water. Preferably the compositions have a pH between about 2 and about 5. The compositions can be in concentrated form or a diluted ready to use form.

The compositions can be a premixed composition or a multi-part system mixed prior to use or at the time of use. For example, a multi-part system, can be prepared with two, three, four, or more parts each having different components, that are combined and mixed prior to or at the time of use. The premixed compositions and multi-part systems are preferably concentrated compositions, which are diluted; however, in some embodiments they may be use concentrations. The concentrated compositions can be in solid, liquid, or gel form. The ready to use forms can be in liquid or gel form. In a preferred embodiment, the concentrated and ready-to-use compositions are liquid. In a preferred embodiment, the composition can be a dissolvable solid. Preferably the dissolvable solid can be added to a drain such that when fluid goes down the drain the solid is partially dissolved forming a use solution that contacts the drain.

In a preferred embodiment, the concentrated compositions are prepared at a concentration that is 10, 9, 8, 7, 6, 5, 4, 3, 2 times the concentration of the desired use solution. In an embodiment, the concentrated composition is diluted at a ratio of between about 1:1 and 1:10. Preferably, the concentrated compositions are diluted at a ratio of about 1:10, 1:9, 1:8, 1:7, 1:6, 1:5, 1:4, 1:3, 1:2, or 1:1.

Preferred embodiments of the compositions are described in Table 1 below.

TABLE 1

| Composition | Preferred | More Preferred | Most Preferred |
|---|---|---|---|
| Enzyme Composition (wt. %) | 0.01-2 | 0.1-1.5 | 0.2-1 |
| Nonionic Surfactant (wt. %) | 0.001-7 | 0.01-5 | 0.1-4.5 |
| Water (wt. %) | 55-99 | 75-97 | 80-95 |
| Additional Ingredients (wt. %) | 0-35 | 0.1-30 | 0.5-25 |

Enzyme Composition

The compositions contain an enzyme composition. The enzyme composition may comprise one or more (e.g., several) enzymes comprising, consisting essentially of, or consisting of a cellulase, an AA9 polypeptide having cellulolytic enhancing activity, a hemicellulase, an esterase, an expansin, a laccase, a ligninolytic enzyme, a pectinase, a peroxidase, a protease, a swollenin, or a combination or mixture thereof. Preferably, the enzyme composition comprises a cellulase. The cellulase is preferably one or more (e.g., several) enzymes comprising, consisting essentially of, or consisting of an endoglucanase, a cellobiohydrolase, a beta-glucosidase, or a combination or mixture thereof. In another aspect, the hemicellulase is preferably one or more (e.g., several) enzymes comprising, consisting essentially of, or consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, a xylosidase, or a combination or mixture thereof.

In an embodiment, the enzyme composition comprises a cellulolytic enzyme composition comprising one or more (e.g., several) enzymes comprising, consisting essentially of, or consisting of a cellobiohydrolase, an endoglucanase, a beta glucosidase an AA9 polypeptide having cellulolytic enhancing activity, or a combination or mixture thereof. In a further embodiment, the enzyme composition comprises one or more cellulases and one or more hemicellulases.

One or more (e.g., several) of the enzymes may be wild-type proteins, recombinant proteins, or a combination of wild-type proteins and recombinant proteins. For example, one or more (e.g., several) enzymes may be native proteins of a cell, which is used as a host cell to express recombinantly the enzyme composition. The enzyme composition may also be a fermentation broth formulation or a cell composition.

The host cell may be any filamentous fungal cell useful in the recombinant production of an enzyme or protein. In an embodiment the enzyme composition is derived from a fungal host cell. In an embodiment the fungal host cell is *Trichoderma reesei*. In one embodiment the enzyme composition is or comprises an expression product of *Trichoderma reesei*.

In one embodiment the enzyme composition is or comprises a cellulolytic enzyme composition derived from *Trichoderma reesei* comprised of *Trichoderma reesei* enzymes having cellulase activity and effective to degrade cellulose to, at least glucose. In one embodiment the enzyme composition has an endoglucanase, and a cellobiohydrolase. In another embodiment the enzyme composition has an endoglucanase, a cellobiohydrolase, and a beta-glucosidase. In a further embodiment the enzyme composition further comprises *A. niger* beta-glucosidase. In a still further embodiment the enzyme composition has an endoglucanase, a cellobiohydrolase, a beta-glucosidase and an AA9 polypeptide having cellulolytic enhancing activity.

In another embodiment the enzyme composition is a cellulolytic enzyme composition comprising an AA9, a beta-glucosidase, a CBHI, and a CBHII. In a further embodiment the cellulolytic enzyme composition further comprises a xylanase and/or a xylosidase. In a further embodiment, the cellulolytic enzyme composition is a cellulolytic enzyme composition derived from *Trichoderma reesei* further comprising a *Penicillium* sp. (*emersonii*) AA9 (GH61) polypeptide having cellulolytic enhancing activity, an *Aspergillus fumigatus* beta-glucosidase variant, an *Aspergillus fumigatus* cellobiohydrolase I, and an *Aspergillus fumigatus* cellobiohydrolase II. In a still further embodiment the cellulolytic enzyme composition further comprises an *Aspergillus fumigatus* xylanase, and an *Aspergillus fumigatus* beta-xylosidase. For example, the enzyme composition is a composition described in WO 2013/028928.

In an embodiment the enzyme composition is or comprises a commercial enzyme preparation. Examples of commercial enzyme preparations suitable for use in the compositions include, but are not limited to, ACCELLERASE® (Danisco US Inc.), ACCELLERASE® XY (Danisco US Inc.), ACCELLERASE® XC (Danisco US Inc.), ACCELLERASE® TRIO (Danisco US Inc.), ALTERNA FUEL 100P (Dyadic), ALTERNA FUEL 200P (Dyadic), CELLIC® CTec (Novozymes A/S), CELLIC® CTec2 (Novozymes A/S), CELLIC® Ctec3 (Novozymes A/S), CELLIC® HTec (Novozymes A/S), CELLIC® HTec2 (Novozymes A/S), CELLIC® HTec3 (Novozymes A/S), CELLUCLAST® (Novozymes A/S), CELLUCLAST CONCENTRATED BG® (Novozymes A/S), CELLUCLEAN CLASSIC 700T® (Novozymes A/S), CELLUZYME™ (Novozymes A/S), CEREFLO® (Novo Nordisk A/S), DEPOL™ 333P (Biocatalysts Limit, Wales, UK), DEPOL™ 740L. (Biocatalysts Limit, Wales, UK), DEPOL™ 762P (Biocatalysts Limit, Wales, UK), DRAIN EASE FLOW™ (Novozymes A/S), ECOPULP® TX-200A (Roal Oy LLC), FIBREZYME® LBR (Dyadic International, Inc.), FIBREZYME® LDI (Dyadic International, Inc.), LAM IN EX® (Danisco US Inc.), HSP 6000 Xylanase (DSM), MULTIFECT® Xylanase (Danisco US Inc.), PULPZYME® HC (Novozymes A/S), ROHAMENT® 7069 W (AB Enzymes), SHEARZYME™ (Novozymes A/S), SPEZYME® CP (Danisco US Inc.), ULTRAFLO® (Novozymes A/S), VISCOSTAR™ 150L (Dyadic International, Inc.), or VISCOZYME® (Novozymes A/S).

Preferably, the compositions include from about 0.01 wt. % to about 2 wt. % enzyme composition, more preferably from about 0.1 wt. % to about 1.5 wt. % enzyme composition, and most preferably from about 0.2 wt. % to about 1 wt. % enzyme composition.

Nonionic Surfactant

The compositions contain a nonionic surfactant having an HLB value between 10 and 22. Preferably, the HLB value is between about 11 and about 20, more preferably between about 12 and about 19, most preferably between about 13 and about 18. Preferably, the surfactant is an alkoxylated surfactant. Suitable alkoxylated surfactants include EO/PO copolymers, capped EO/PO copolymers, alcohol alkoxylates, capped alcohol alkoxylates, mixtures thereof, or the like. Preferred surfactants, including, but are not limited to, alcohol ethoxylates, polyethylene glycol sorbitan ester, polyethylene glycol ether, polyoxyethylene ether, a poly(propylene glycol)-block-poly(ethylene glycol)-block-poly(propylene glycol), poly(ethylene glycol)-block-poly(propylene glycol)-block-poly(ethylene glycol), or mixture thereof so long as the surfactant selected has an HLB value between 10 and 22. Suitable alkoxylated surfactants for use as solvents include EO/PO block copolymers, such as the Pluronic and reverse Pluronic surfactants; alcohol alkoxylates, such as Dehypon LS-54 (R-(EO)$_5$(PO)$_4$) and Dehypon LS-36 (R-(EO)$_3$(PO)$_6$); and capped alcohol alkoxylates, such as Plurafac LF221 and Tegoten EC11; mixtures thereof, or the like.

Preferred surfactants include, but are not limited to, polyethylene glycol sorbitan monolaurate (commercially available as Tween 20 from Sigma-Aldrich), polyethylene glycol sorbitan monooleate (commercially available as Tween 80 from Sigma-Aldrich), polyethylene glycol tert-octylphenyl ether (commercially available as Triton X-100 from Sigma-Aldrich), polyethylene glycol trimethylnonyl ether (commercially available as Tergitol TMN-6 from Sigma-Aldrich), poly(propylene glycol)-block-poly(ethylene glycol)-block-poly(propylene glycol) (commercially available as Pluronic 10R5 from Sigma-Aldrich, preferably having an average molecular weight of 1950), polyoxyethylene (23) lauryl ether (commercially available as Brij L23 from Sigma-Aldrich), and mixtures thereof.

Preferably, the compositions include from about 0.001 wt. % to about 7 wt. % nonionic surfactant, more preferably from about 0.01 wt. % to about 5 wt. % nonionic surfactant, still more preferably from about 0.1 wt. % to about 4.5 wt. %, and most preferably from about 1 wt. % to about 4 wt. % nonionic surfactant.

pH

In an acidic embodiment, the compositions preferably have a pH equal to or less than about 5, more preferably, between about 2 and about 4.75, most preferably between about 3 and about 4.5. It has been found that the compositions lose stability at a pH of above 5 with most buffers and stabilizers. However, using the buffer CAPS it was found that the compositions perform well at a pH of between about 8 and about 11, more preferably between about 9 and about 10.5, most preferably at a pH of about 10. In an embodiment having a multi-part system combined prior to or at the time of use, the compositions can be prepared with a pH between about 2 and about 11. However, if the pH is between about 4.5 and about 8, the stability of the compositions may require use fairly quickly after combining the different parts. Thus, in a preferred embodiment having a pH between 4.5 and 8, the compositions are used no more than 2 hours, 90 minutes, 60 minutes, 45 minutes, 30 minutes, 25 minutes, 20 minutes, 15 minutes, 10 minutes, 5 minutes, 4 minutes, 3 minutes, 2 minutes, or 1 minute, after combination.

Water

The compositions contain water. In a preferred embodiment comprising water as a carrier, the water is deionized water or softened water.

The water typically makes up the remaining volume after the addition of all other ingredients. Preferably, the compositions include from about 55 wt. % to about 99 wt. % water, more preferably from about 75 wt. % to about 97 wt. % water, and most preferably from about 80 wt. % to about 95 wt. % water.

Additional Optional Ingredients

The compositions can include a number of optional ingredients in various embodiments. Many additional optional ingredients can be added to provide desired properties to the compositions. Optional ingredients can include, but are not limited to, a buffering agent, a colorant, an additional enzyme, a fragrance, a pH modifier, a stabilizing agent, an additional surfactant, a thickening agent, and mixtures thereof.

Buffering Agent

The compositions can optionally include a buffering agent. As used herein the term "buffer" and "buffering agent" are synonymous. Preferred buffering agents include, but are not limited to, N-cyclohexyl-3-aminopropanesulfonic acid (CAPS), N-cyclohexyl-2-aminoethanesulfonic acid (CHES), N-(2-hydroxyethyl)piperazine-N'-(4-butanesulfonic acid) (HEPBS), 4-(2-hydroxyethyl)-1-piperazineethanesulfonic acid (HEPES), 3-[4-(2-hydroxyethyl)-1-piperazinyl]propanesulfonic acid (HEPPS), 3-(N-morpholino) propanesulfonic acid (MOPS), 2-(N-morpholino) ethanesulfonic acid (MES), pH modifiers (discussed below), tris(hydroxymethyl)aminomethane (Tris), and mixtures thereof. Most preferred buffers, include CAPS, CHES, citric acid and its salts (including in particular sodium citrate), and mixtures thereof. Specifically, CAPS and CHES are most preferred for alkaline pH and citric acid, citrate, acetic acid, and acetate are most preferred for acidic pH.

Preferably, the compositions include from about 0.1 wt. % to about 5 wt. % buffering agent, more preferably from about 0.5 wt. % to about 3 wt. % buffering agent, and most preferably from about 1 wt. % to about 2 wt. % buffering agent.

Colorant

The compositions can optionally comprise a colorant. The colorant can be a dye or an additive that provides a visible color or color change. Preferred colorants, including, but are not limited to, copper(II) salts, Direct Blue 86, available from Mac Dye-Chem Industries, Ahmedabad, India; Fastusol Blue, available from Mobay Chemical Corporation, Pittsburgh, Pa.; Acid Orange 7, available from American Cyanamid Company, Wayne, N.J.; Basic Violet 10 and Sandolan Blue/Acid Blue 182, available from Sandoz, Princeton, N.J.; Acid Yellow 23, available from Chemos GmbH, Regenstauf, Germany; Acid Yellow 17, available from Sigma Chemical, St. Louis, Mo.; Sap Green and Metanil Yellow, available from Keyston Analine and Chemical, Chicago, Ill.; Acid Blue 9, available from Emerald Hilton Davis, LLC, Cincinnati, Ohio; Hisol Fast Red and Fluorescein, available from Capitol Color and Chemical Company, Newark, N.J.; and Acid Green 25, Ciba Specialty Chemicals Corporation, Greenboro, N.C.

Preferably the colorant can be in a concentration between about 0 wt. % and about 2 wt. %, more preferably between about 0.001 wt. % and about 1 wt. %.

Additional Enzyme

The compositions can optionally include an additional enzyme. Suitable additional enzymes, include, but are not limited to, a protease, a xylanase, a nuclease, and mixtures thereof. If the compositions contain an additional enzyme, it is preferably in a concentration from about 0.01 wt. % to about 2 wt. %, more preferably from about 0.1 wt. % to about 1.5 wt. %, and most preferably from about 0.5 wt. % to about 1 wt. %.

Fragrance

The compositions can optionally comprise a fragrance. Preferred fragrances include, but are not limited to, terpenoids such as citronellol, aldehydes such as amyl cinnamaldehyde, a jasmine such as C1S-jasmine or jasmal, vanillin, and the like. Preferably the fragrance can be in a concentration between about 0 wt. % and about 1 wt. %, more preferably between about 0.01 wt. % and about 1 wt. %.

pH Modifier

The compositions can include a pH modifier to adjust the pH or act as a buffer. Suitable pH modifiers can include water soluble acids. Preferred acids can be organic and/or inorganic acids and their salts that are water soluble.

Preferred inorganic acids include, but are not limited to, boric acid, hydrobromic acid, hydrochloric acid, hydrofluoric acid, hydroiodic acid, hypophosphorous acid, phosphoric acid, phosphorous acid, polyphosphoric acid, sulfamic acid, sulfuric acid, sulfurous acid, sodium bisulfate, sodium bisulfite, their salts and mixtures thereof.

Preferred organic acids include, but are not limited to, acetic acid, acrylic acids, adipic acid, benzoic acid, butyric acid, caproic acid, citric acid, formic acid, fumaric acid, gluconic acid or its precursor glucono-δ-lactone, glutaric acid, hydroxy acetic acid, isophthalic acid, lactic acid, lauric acid, maleic acid, malic acid, malonic acid, palmitic acid, pimelic acid, polymaleic-acrylic acids, polyacrylic acids, propionic acid, sebacic acid, stearic acid, suberic acid, succinic acid, tartaric acid, terephthalic acid, uric acid, valeric acid, their salts and mixtures thereof. Preferred acid salts include, but are not limited to, acetic acid salts, citric acid salts, formic acid salts, and mixtures thereof.

Preferably, the compositions include from about 0.1 wt. % to about 5 wt. % pH modifier, more preferably from about 0.5 wt. % to about 3 wt. % pH modifier, and most preferably from about 1 wt. % to about 2 wt. % pH modifier.

Stabilizing Agent

The compositions can optionally comprise a stabilizing agent. Preferred stabilizing agents include, but are not limited to, borate, calcium/magnesium ions, glycerol, polyethylene glycol 200, polyethylene glycol 400, propylene glycol, sucrose, and mixtures thereof. When the compositions include a stabilizing agent, it can be included in an amount that provides the desired level of stability to the composition.

Preferably, the compositions include from about 0.01 wt. % to about 30 wt. % stabilizing agent, more preferably from about 0.5 wt. % to about 25 wt. % stabilizing agent, and most preferably from about 1 wt. % to about 25 wt. % stabilizing agent.

Additional Surfactant

In some embodiments, the compositions include an additional surfactant besides the nonionic surfactant having an HLB between 10 and 22. Additional surfactants suitable for use in the compositions include, but are not limited to, anionic surfactants, cationic surfactants, nonionic surfactants, and zwitterionic surfactants. Preferred additional surfactants, include, but are not limited to, nonionic seed oil surfactants, such as the alcohol ethoxylate Ecosurf SA-9 (commercially available from DOW Chemical), cocamidopropyl betaine (commercially available as Amphosol CG from Stepan), cocamidopropyl hydroxysultaine (commercially available as Macham 50-SB from Solvay), alkyl polyglucosides, including, for example decyl glucoside (commercially available as APG 325N from BASF), cocoamine oxide (commercially available as Barlox 12 from Lonza), sodium xylene sulfonate, ethylene oxide/propylene oxide block copolymers, such as the Pluronic surfactant line available from BASF (such as Pluronic 25R and Pluronic 10R5), cocamidopropyl hydroxysultaine (commercially available as Mackam 50-SB from Solvay), and mixtures thereof.

When the compositions include an additional surfactant, preferably it is in a concentration from about 0.01 wt. % to about 5 wt. %.

Thickening Agent

The compositions can optionally include a thickening agent. A wide variety of thickening agents can be included. Preferred thickening agents can be organic or inorganic. When a thickening agent is included, it is preferably in an amount between about 0.01 wt. % and about 5 wt. %.

Preferred organic thickening agents include, but are not limited to, acrylic copolymers, carboxyvinyl polymers, corn starch, crosslinked polyacrylic acid-type thickening agents, fatty acid thixotropic thickeners, guar gum, guar hydroxy propyltrimonium chloride, polyacrylate polymers, poly (methylvinylether/maleic) anhydride polymers, and mixtures thereof.

As used herein, "polyacrylic acid-type" is intended to refer to water soluble homopolymers of acrylic acid or methacrylic acid or water-dispersible or water-soluble salts, esters and amides thereof, or water-soluble copolymers of these acids or their salts, esters or amides with each other or with one or more ethylenically unsaturated monomers, such as styrene, maleic acid, maleic anhydride, 2-hydroxyethylacrylate, acrylonitrile, vinyl acetate, ethylene, propylene, or the like. Preferably, the polyacrylic thickening agent is one of the crosslinked polyacrylic acid-type thickening agents commercially available as CARBOPOL™. The CARBOPOL™ resins, also known as carbomer resins, are hydrophilic, high molecular weight, crosslinked acrylic acid polymers. The CARBOPOL™ resins are crosslinked with a polyalkenyl polyether, such as a polyalkyl ether of sucrose having an average of 5.8 alkyl groups per molecule of sucrose. Other suitable carbomer thickening agents include the PNC carbomers.

Suitable fatty acid thixotropic thickeners, include, but are not limited to, higher aliphatic fatty monocarboxylic acids having from about 8 to about 22 carbon atoms, inclusive of the carbon atom of the carboxyl group of the fatty acid. The aliphatic radicals are saturated and can be straight or branched. Mixtures of fatty acids may be used, such as those derived from natural sources, such as tallow fatty acid, coco fatty acid, soya fatty acid, etc., or from synthetic sources available from industrial manufacturing processes.

Examples of the fatty acids which can be used as thickeners include, for example, decanoic acid, lauric acid, dodecanoic acid, palmitic acid, myristic acid, stearic acid, oleic acid, eicosanoic acid, tallow fatty acid, coco fatty acid, soya fatty acid and mixtures of these acids. The metal salts of the above fatty acids can also be used in as thixotropic thickener agents, such as salts of the monovalent and polyvalent metals such as sodium, potassium, magnesium, calcium, aluminum and zinc. Suitable metal salts, include, but are not limited to, aluminum salts in triacid form, e.g., aluminum tristearate, $Al(OCOC_{17}H_{35})_3$, monoacid salts, e.g., aluminum monostearate, $Al(OH)_2(OCOC_{17}H_{35})$ and diacid salts, e.g. aluminum distearate, $Al(OH)(OCOC_{17}H_{35})_2$, and mixtures of two or three of the mono-, di- and triacid salts can be used for those metals, e.g., Al, with valences of +3, and mixtures of the mono- and diacid salts can be used for those metals, e.g., Zn, with valences of +2.

The thickening agent used can also be any one of a number of natural or synthetic inorganic materials, such as clays, silicas, aluminas, titanium dioxide (pyrogenic) and calcium and/or magnesium oxides. All of these materials are readily available from commercial sources.

Various types of clays which are useful include kaolins such as kaolinite, dicktite, nacrite, halloysite and endillite; serpentine clays such as chrysotile and amesite; smectites such as montmorillonite (derived from bentonite rock), beidellite, nontronite, hectorite, saponite and sauconite; illites or micas; glauconite; chlorites and vermiculites; attapulgite and sepiolite. Mixed layer clays exhibiting intercalation of mineral sandwiches with one another may be used, such as, for example, mixed-layer clay mineral sheets of illite interspersed randomly or regularly with montmorillonite, or chlorite with one of the other types of clay, such as vermiculite. Other useful clays include amorphous clays, such as allophone and imogolite, and high-alumina clay minerals such as diaspore, boehmite, bibbsite and cliachite. Various types of silicas which are useful include diatomite, precipitated silica and fumed silica. Various types of aluminas may be used, as well as various types of calcium and magnesium oxides.

Methods of Preparing the Compositions

The compositions can be prepared by adding and mixing the desired ingredients. Preferably the ingredients are mixed until they are homogeneous or substantially homogenous. The compositions can be prepared manually or by a system that adds the components in desired quantities to achieve a particular concentration of ingredients. In a preferred embodiment, the compositions are prepared as a concentrated composition and diluted on site prior or during use. In a preferred embodiment, the ingredients are mixed at the time of use prior to contacting a surface or at the time of contacting a surface to be cleaned. The compositions can be prepared as a multi Methods of Using the Compositions The compositions can be used by contacting a hard surface, preferably a drain, with the composition. Typically, the hard surface has a bacterial cellulose deposit or may be susceptible to the development of a bacterial cellulose deposit. Such hard surfaces, including, but are not limited to, drains, floors, sinks, beverage tower fluid lines, or combination thereof. In an aspect of the method of use, the composition can be allowed to contact the hard surface for a sufficient time to at least partially degrade the bacterial cellulose deposit, whereby the at least partially degraded material is removed from the hard surface. In another aspect of the method of use, the composition is allowed to coat the hard surface to prevent or at least reduce the development of a bacterial cellulose deposit.

In one embodiment of the present method used to remove or prevent bacterial cellulose deposits is added directly to a hard surface, preferably a drain system through an opening in the system, such as a floor drain or any other opening that will allow access to the drain interior. Preferably the composition is in contact with the hard surface for a time prior to use or rinsing of at least about 1 second, 2 seconds, 3 seconds, 4 seconds, 5 seconds, 6 seconds, 7 seconds, 8 seconds, 9 seconds, 10 seconds, 11 seconds, 12 seconds, 13 seconds 14 seconds, 15 seconds, 20 seconds, 25 seconds, 30 seconds, 35 seconds, 40 seconds, 45 seconds, 50 seconds, 55 seconds, 1 minute, 90 seconds, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 20 minutes, 25 minutes, 30 minutes, 45 minutes, 1 hour, 2 hours, 3, hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 30 hours, 36 hours, 48 hours, 60 hours, 72 hours.

Optionally, the hard surface can be rinsed after allowing the composition to contact the hard surface for sufficient time. In a preferred embodiment, the hard surface is not rinsed after contact with the composition. In another preferred embodiment, the hard surface is rinsed with water. The water can have a temperature between 10° C. and about 100° C., preferably between about 25° C. and about 90° C., more preferably between about 35° C. and about 80° C.

The method of use requires no particular mode of contacting the composition to the bacterial cellulose deposit to be removed, provided the contact takes place for a time sufficient to allow at least partial degradation of the bacterial cellulose deposit. Optionally, the bacterial cellulose can be removed with minimal mechanical or manual effort, such as by flushing or rinsing, by gentle mechanical agitation, or by continued use of the compositions described herein. Preferably, the composition is permitted to contact the deposits for at least two to three hours.

The drain cleaners, compositions, and methods can be applied to effect both prevention and removal of bacterial cellulose deposits. When used to clean drain pipes, such as soft drink and alcoholic beverage station drain pipes, the condition of the drain must be ascertained, i.e., whether the drain is fully or partially clogged. If fully clogged, the drain can be partially unblocked, typically by mechanical means such as snaking, rotor rooting, water jetting, etc., to allow the composition to contact as much of the deposited bacterial cellulose as possible. However, it is also possible to apply the compositions to a fully clogged drain in small amounts repeatedly as it degrades the bacterial cellulose deposit.

In a preferred embodiment, the compositions provide a synergistic degradation of bacterial cellulose deposits. Further, they can provide removal of malodor and have a cidal effect on insects, particularly flies, that tend to feed off of bacterial cellulose deposits.

All publications and patent applications in this specification are indicative of the level of ordinary skill in the art to which this disclosure pertains. All publications and patent applications are herein incorporated by reference to the same extent as if each individual publication or patent application was specifically and individually indicated as incorporated by reference.

EXAMPLES

Embodiments of the present disclosure are further defined in the following non-limiting Examples. It should be understood that these Examples, while indicating certain embodiments, are given by way of illustration only. From the above discussion and these Examples, one skilled in the art can ascertain the essential characteristics of the compositions and methods, and without departing from the spirit and scope thereof, can make various changes and modifications to adapt it to various usages and conditions. Thus, various modifications of the embodiments, in addition to those shown and described herein, will be apparent to those skilled in the art from the foregoing description. Such modifications are also intended to fall within the scope of the appended claims.

The materials used in the following Examples are provided herein:

Amphosol CG: an amphoteric surfactant, cocamidopropyl betaine, available from Stepan.

APG 325N: a nonionic surfactant, alkyl polyglucoside (decyl glucoside) having an HLB of about 13, available from BASF Corp.

Barlox 12: a zwitterionic surfactant, cocoamine oxide, available from Lonza.

Bioterge AS-40K: an anionic surfactant, sodium C14-16 alpha olefin sulfonate, available from Stepan.

Brij L23: a nonionic surfactant, polyoxyethylene (23) lauryl ether having an HLB of 17, available from Sigma-Aldrich.

Biological Formula 2-24 Instant *Drosophila* Medium: a culture medium available from Carolina.

Cellulase C: an exemplary enzyme composition comprising a cellulase enzyme obtained from Novozymes. Cellulase C comprises between 70 wt. % and about 75 wt. % water, between 10 wt. % and about 20 wt. % cellulase, between about 5 wt. % and about 15 wt. % sorbitol, and less than 1 wt. % proxel.

CELLUCLAST CONCENTRATED BG: an exemplary enzyme composition available from Novozymes.

CELLUCLEAN CLASSIC 700T: an exemplary enzyme composition available from Novozymes.

DRAIN EASE FLOW: an exemplary enzyme composition comprising a cellulase enzyme obtained from Novozymes. DRAIN EASE FLOW comprises water, a polysaccharide, a cellulase, sodium benzoate, and potassium sorbate. The water comprises between about 40 wt. % and about 50 wt. % of the enzyme composition. The polysaccharide comprises between about 25 wt. % and about 35 wt. % of the enzyme composition. The polysaccharide comprises sucrose, glucose, or a mixture thereof. The cellulase comprises between about 20 wt. % and about 25 wt. % of the enzyme composition.

Ecosurf SA-9: a nonionic alcohol ethoxylate seed oil surfactant having an HLB of 11-13, available from DOW Chemical.

Mackam 50-SB: a zwitterionic surfactant, cocamidopropyl hydroxysultaine, available from Solvay.

PEG 200: a polyethylene glycol available from a number of commercial sources including, Sigma-Aldrich.

Pluronic F108: a nonionic surfactant, ethylene oxide and propylene oxide block copolymer having an HLB greater than 24, available from BASF.

Pluronic L31: a nonionic surfactant, ethylene oxide and propylene oxide block copolymer having an HLB of 1-7, available from BASF.

Pluronic 10R5: a nonionic surfactant, poly(propylene glycol)-block-poly(ethylene glycol)-block-poly(propylene glycol) having an HLB of 12-18, available from Sigma-Aldrich.

Pluronic 25R: a nonionic surfactant, ethylene oxide and propylene oxide block copolymer having an HLB of 7-12, available from BASF.

Sodium xylene sulfonate (SXS), an anionic surfactant available from multiple commercial sources.

Tergitol NP-12: a nonionic nonylphenol ethoxylate having an HLB of 13.8, available from DOW Chemical.

Tergitol TMN-6: a nonionic surfactant, polyethylene glycol trimethylnonyl ether having an HLB of 13.1, available from DOW Chemical.

Triton X-100: a nonionic surfactant, polyethylene glycol tert-octylphenyl ether having an HLB of 13.5, available from Sigma-Aldrich.

Tween 20: a nonionic surfactant, polyethylene glycol sorbitan monolaurate having an HLB of 16.7, available from Sigma-Aldrich.

Tween 80: a nonionic surfactant, polyethylene glycol sorbitan monooleate having an HLB of 15, available from Sigma-Aldrich.

Additional ingredients available from a number of sources include, citric acid, glycerol, sodium citrate, and water (5 grain). Concentration percentages of ingredients provided in the Examples below are in weight percent unless indicated as percent active.

Example 1

In order to test interactions between enzyme compositions comprising cellulase(s) and detergent components the "Cellulase catalyzed hydrolysis of bacterial cellulose" method was used. For this method, the sugar snake is weighed before and after treatment with the listed chemistry. The percent sugar snake degraded after two hours was calculated and recorded. The general formulation is listed in Table 2 below.

TABLE 2

| Component | Species | Concentration (wt. %) |
| --- | --- | --- |
| Buffer | Citric Acid (50%) | 1.12% |
| Buffer | Trisodium Citrate | 0.6% |
| Surfactant | See Table 3 | 0-4% |
| Enzyme | DRAIN EASE FLOW | 0.5% |
| Water | 5 grain | Q.S. |

Aside from enzyme RM, all percentages are percent active concentrations. The type of surfactant was varied and compared to the control formulation which did not contain surfactant. If the amount of sugar snake degraded after a set time was statistically greater than the control reaction across replicate tests it was deemed synergistic. If the amount of degradation was comparable the surfactant interaction was deemed compatible, and if the amount of degradation was less than the control the surfactant interaction was deemed less favorable. The results are provided below in Table 3 showing the percent degradation of the sugar snake an assessment of the enzyme compatibility.

TABLE 3

| Surfactant | HLB | Degradation Increase (%) | Compatibility Rating |
| --- | --- | --- | --- |
| Pluronic L31 | 1-7 | 0.22 | Compatible |
| Pluronic 10R5 | 12-18 | 20 | Synergistic |
| Tergitol TMN-6 | 13.1 | 20.6 | Synergistic |
| Triton X-100 | 13.5 | 30.1 | Synergistic |
| Tween 80 | 15 | 21.9 | Synergistic |
| Tween 20 | 16.7 | 20.4 | Synergistic |
| Brij L23 | 17 | 10.6 | Synergistic |
| Pluronic F108 | >24 | −0.9* | Compatible |

*Pluronic F108 was not statistically different than the no-surfactant control

The results from Table 3 are also shown in FIG. 1. As can be seen in Table 3 and in FIG. 1, nonionic surfactants with HLB values ranging from about 10-22 showed enhanced performance, with unexpected synergy in the range of about 13 HLB to about 18 HLB. The data also shows that Pluronic L31 (HLB 1-7) and Pluronic F108 (>24) were not statistically different from the no-surfactant control.

Example 2

Another wider test was completed using a method in which a piece of sugar snake (weight previously recorded) was incubated in chemistry containing surfactant. After a set time, the remaining sugar snake was removed and quantified by water displacement in a graduated cylinder. After treatment, sugar snake degradation was determined by subtracting the volume (mL) of water displacement from the starting weight (grams). Each variation was compared to a control where the surfactant was omitted. The same three terms as above (synergistic, compatible, and less favorable) were used to identify the enzyme compatibility of each surfactant. Results are shown in Table 4.

TABLE 4

| Surfactant | Concentration (wt. %) | pH | Incubation Time (hr) | Percent Degradation | Compatibility Rating |
| --- | --- | --- | --- | --- | --- |
| Tergitol NP-12 | 4 | 4 | 24 | 61 | Less Favorable |
| Ecosurf SA-9 | 4 | 4 | 8 | 85 | Compatible |
| Amphosol CG | 4 | 4 | 8 | 54 | Compatible |
| Mackam 50-SB | 4 | 4 | 8 | 51 | Compatible |
| Bioterge AS-40K | 4 | 4 | 8 | 27 | Less Favorable |
| APG 325N | 4 | 4 | 7 | 85 | Compatible |
| APG 325N | 4 | 10 | 7 | 43 | Less Favorable |
| Barlox 12 | 4 | 4 | 7 | 85 | Compatible |
| Barlox 12 | 4 | 10 | 7 | 16 | Less Favorable |
| SXS | 4 | 4 | 7 | 85 | Compatible |
| SXS | 2 | 4 | 7 | 11 | Compatible |
| Pluronic 25R | 4 | 4 | 8 | 58 | Compatible |

Example 3

Figure 2:
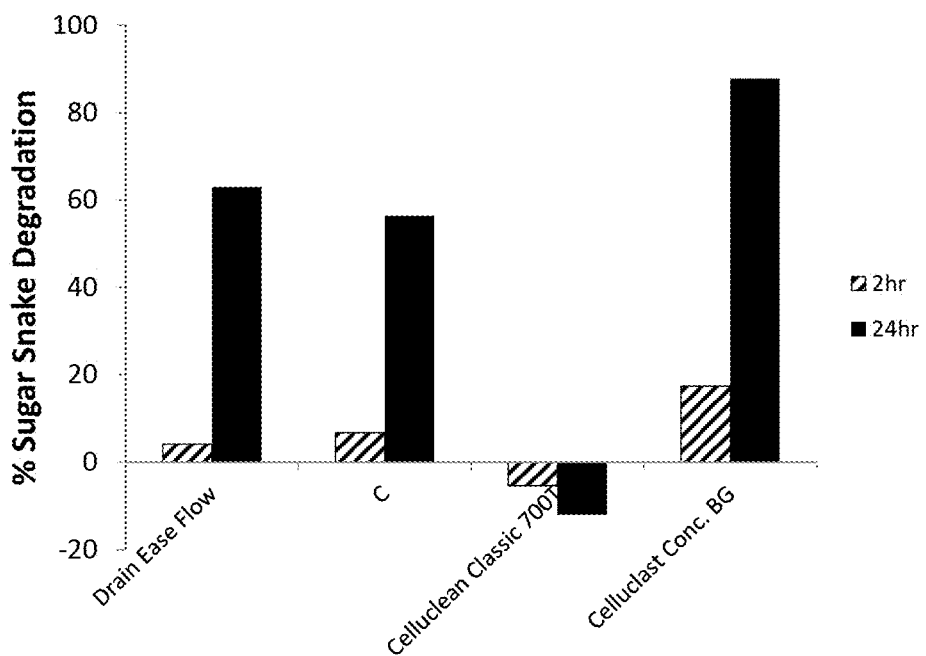
FIG. 2 is a bar graph from the testing in Example 3 evaluating the baseline sugar snake degradation performance of four different enzyme compositions comprising a cellulase after 2 hours of contact time and 24 hours of contact time.

Multiple enzyme compositions comprising a cellulase were evaluated to determine sugar snake degradation performance as a baseline without potential surfactant synergy to assess the role of the enzyme composition versus improvement based on surfactant synergy. Compositions were prepared with 0.5 wt. % enzyme composition, 1.7 wt. % sodium citrate buffer, and water at a pH of 4.25. The four enzyme compositions tested were obtained from Novozymes and included: DRAIN EASE FLOW, CELLUCLEAN CLASSIC 700T, CELLUCLAST CONCENTRATED BG, and Cellulase C. A sugar snake of equal mass was measured and the cleaning compositions were applied to it. The percent degradation of the sugar snake (based on mass) was evaluated after 2 hours of contact and after 24 hours of contact. The percent degradation is shown in FIG. 2 where 100 indicates 100% degradation. As can be seen in FIG. 2, CELLUCLAST CONCENTRATED BG provided the best sugar snake degradation at both the 2-hour time and 24-hour time. DRAIN EASE FLOW and Cellulase C performed substantially similar and CELLUCLEAN CLASSIC 700T did not appear to degrade the sugar snake at all.

Example 4

The three enzyme compositions that had a good baseline were tested in an exemplary cleaning composition containing Tween 20 to assess which would exhibit synergistic performance with a surfactant. Compositions were prepared with 0.5 wt. % enzyme composition, 1.7 wt. % sodium citrate buffer, 2 wt. % Tween 20, and water at a pH of 4.25. The three enzyme compositions tested were DRAIN EASE FLOW, CELLUCLAST CONCENTRATED BG, and Cellulase C, all from Novozymes. Control compositions were also prepared without the surfactant (Tween 20) having 0.5 wt. % enzyme composition, 1.7 wt. % sodium citrate buffer, and water at a pH of 4.25. A sugar snake of equal mass was measured and the cleaning compositions were applied to it. The percent degradation of the sugar snake (based on mass) was evaluated after 2 hours of contact and after 18 hours of contact. The percent degradation is shown in FIGS. 3A-3C where 100 indicates 100% degradation.

Figure 3A:
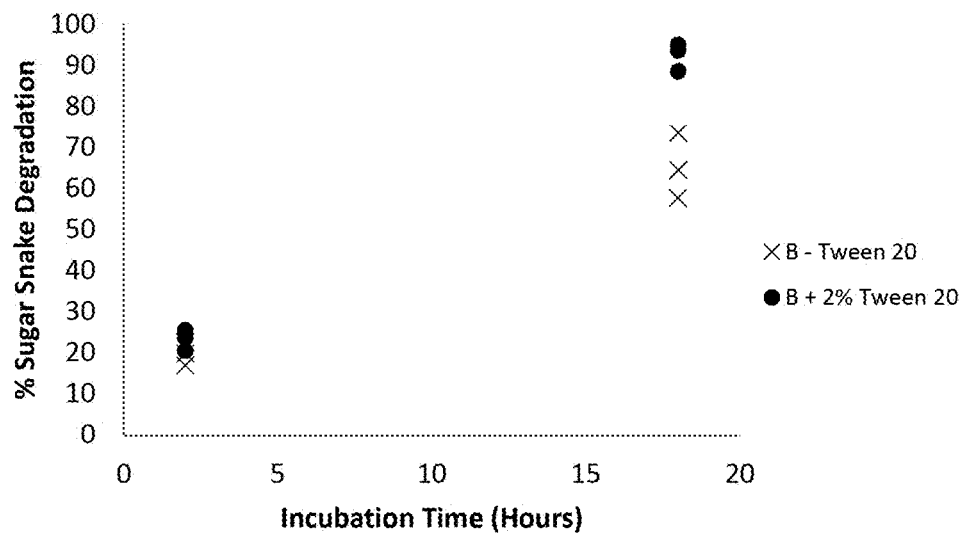
FIG. 3A is a scatter plot from Example 4 comparing the percent degradation of a sugar snake with DRAIN EASE FLOW versus DRAIN EASE FLOW and Tween-20.
Figure 3B:
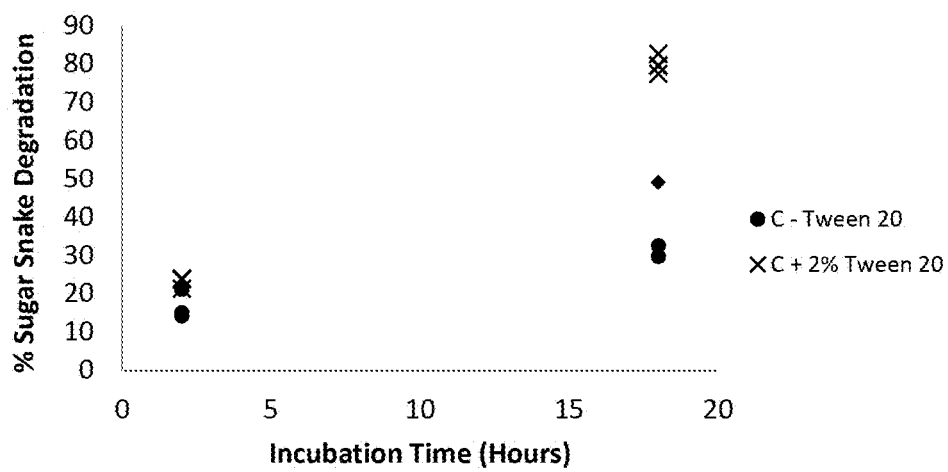
FIG. 3B is a scatter plot from Example 4 comparing the percent degradation of a sugar snake with Cellulase C versus Cellulase C and Tween-20.
Figure 3C:
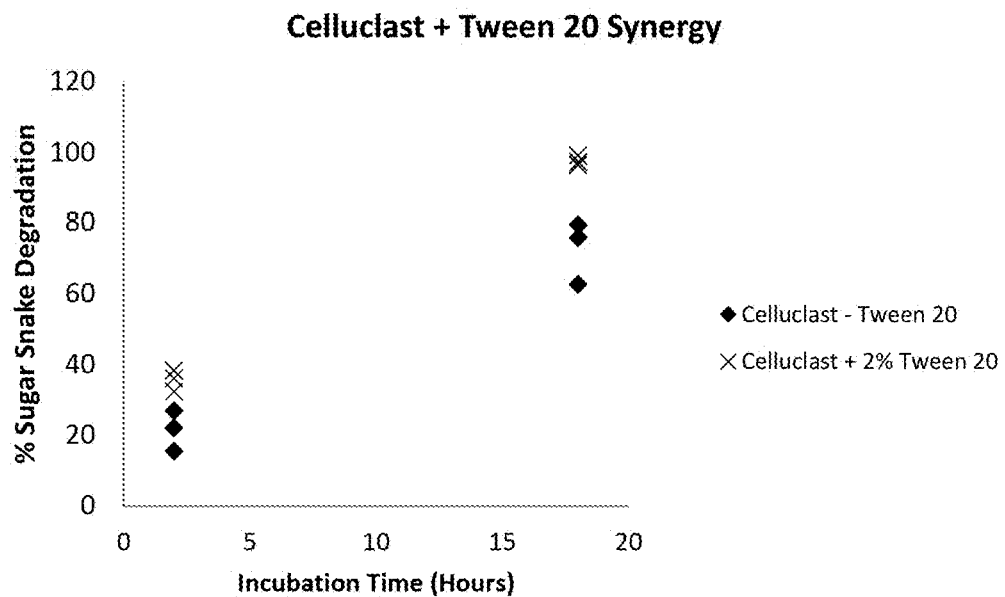
FIG. 3C is a scatter plot from Example 4 comparing the percent degradation of a sugar snake with CELLUCLAST CONCENTRATED BG versus CELLUCLAST CONCENTRATED BG and Tween-20.

As can be seen in FIGS. 3A-3C, all three of the enzyme compositions demonstrated synergistic improvement with the surfactant added. DRAIN EASE FLOW and CELLUCLAST CONCENTRATED BG both degraded the sugar snake entirely after 18 hours. The observed synergy became more apparent with increased incubation time. T-tests were done on all the data to assess statistical improvement. The results of the t-test are summarized in Table 5.

TABLE 5

| Cellulase RM | Difference (+/−2% Tween 20) | p value | 95% Confidence Interval |
|---|---|---|---|
| Drain Ease Flow | −27.30% | 0.032 | −48.8-5.9 |
| Cellulase C | −42.70% | 0.02 | −69.3, 16.0 |
| Celluclast Conc BG | −25.00% | 0.039 | −47.1, −3.0 |

The T-test analysis shows that each sample had a statistical difference between +/−2% Tween 20 at 18 hours incubation time.

Example 5

Figure 4:
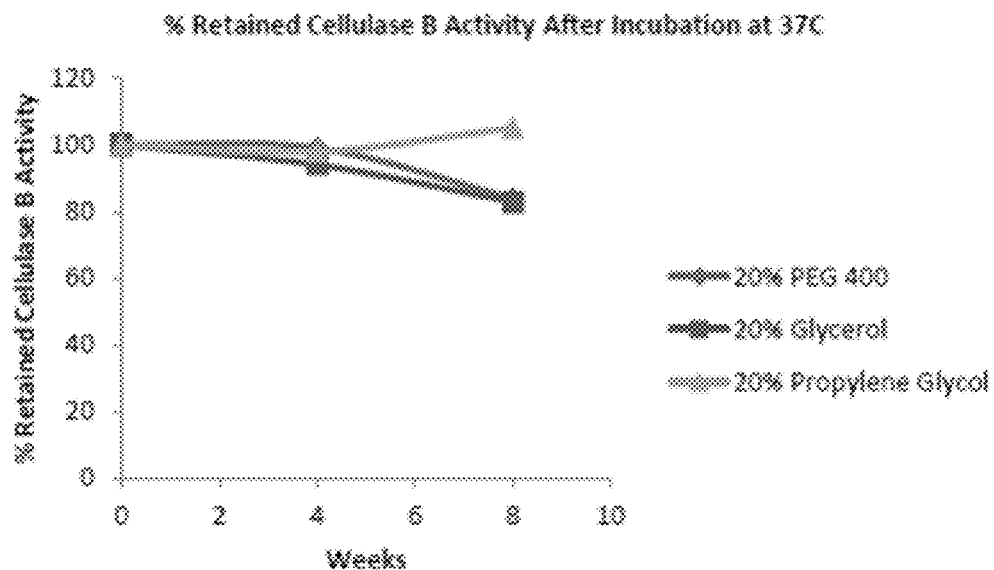
FIG. 4 is a line graph form Example 5 showing the enzyme stability by retained activity of an exemplary cleaning composition with differing stabilizers after incubation at 37° C. at 2-week intervals over an 8-week period.

Enzyme stability was tested in cleaning compositions prepared with differing stabilizers. All test compositions were prepared containing 0.5% DRAIN EASE FLOW, 2% Tween 20, and 1.8% sodium citrate buffer in water prepared at a pH of about 4.5 Enzyme stability was assessed by an activity assay. The results are provided in FIG. 4. Formulations containing 20% PEG 400 and 20% glycerol showed 84% and 83% retention of DRAIN EASE FLOW activity after 8 weeks at 37° C. Formulations containing 20% propylene glycol showed 100% retention of DRAIN EASE FLOW activity under the same conditions. Indicating the stabilizers did provide enzyme stability and retention.

Example 6

DRAIN EASE FLOW performance was also assessed using the "Cellulase catalyzed hydrolysis of bacterial cellulose" test at increasing stabilizer concentrations. The initial screening was done using about 1 gram of sugar snake dosed at 20 mL/gram chemistry. The relative enzyme performance was determined at each concentration by comparing the performance to control formulations lacking stabilizer. The percent degradation is shown in FIG. 5 where 100 indicates 100% degradation and N/A indicates immediate precipitation upon the addition of the enzyme. Of all the potential stabilizers tested, glucose showed the highest inhibition whereas PEG 200 had the lowest impact on performance. After incubating sugar snake for 24 hours in exemplary cleaning compositions, the samples were visually assessed for amount of sugar snake remaining. Formulations containing 0.5% DRAIN EASE FLOW, 2% Tween 20, and 1.8% sodium citrate buffer in water prepared at a pH of about 4.5 were found to fully degrade the sugar snake. Formulations containing 20% PEG 200, 20% PEG 400, and 20% sucrose, respectively, were also each found to fully degraded the sugar snake. Formulations containing other stabilizers did not result in complete degradation of sugar snake even after 24 hours despite fairly high performance after 2 hours.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. A composition for cleaning bacterial cellulose deposits comprising:
   from about 0.01 wt. % to about 2 wt. % of an enzyme composition comprising one or more of the following: a cellulase, an AA9 polypeptide having cellulolytic enhancing activity, a hemicellulase, an esterase, an expansin, a laccase, a ligninolytic enzyme, a pectinase, a peroxidase, a protease, and a swollenin;
   from about 0.01 wt. % to about 7 wt. % of a nonionic surfactant, wherein the nonionic surfactant has an HLB value between 13 and 18;
   from about 0.01 wt. % to about 30 wt. % of a stabilizing agent comprising glycerol, polyethylene glycol 200, polyethylene glycol 400, propylene glycol, sucrose, or a mixture thereof; and
   from about 55 wt. % to about 97 wt. % of water;
   wherein the composition has a pH between about 2 and about 11.

2. The composition of claim 1, wherein the nonionic surfactant an alcohol ethoxylate, a polyethylene glycol sorbitan ester, a polyethylene glycol ether, a polyoxyethylene ether, a poly(propylene glycol)-block-poly(ethylene glycol)-block-poly(propylene glycol), a poly(ethylene glycol)-block-poly(propylene glycol)-block-poly(ethylene glycol), or mixture thereof.

3. The composition of claim 1, wherein the composition further comprises a buffering agent at a concentration from about 0.1 wt. % to about 5 wt. %; wherein the buffering agent comprises CAPS, CHES, HEPBS, HEPES, HEPPS, MOPS, MES, Tris, an organic acid or salt thereof, an inorganic acid or salt thereof, or a mixture thereof.

4. The composition of claim 3, wherein the buffering agent comprises acetic acid, acetate, citric acid, citrate, CAPS, CUES, or mixture thereof.

5. The composition of claim 1, wherein the cellulase comprises a cellobiohydrolase, an endoglucanase, a beta glucosidase, or a combination or mixture thereof.

6. The composition of claim 5, wherein the cellulase is derived from an expression product of *Trichoderma reesei*.

7. The composition of claim 1, wherein the composition has a pH less than about 5.

8. The composition of claim 1, wherein the composition is a multi-part system.

9. The composition of claim 1, wherein the composition further comprises a colorant an additional enzyme, a fragrance, an additional surfactant, a thickening agent, or a mixture thereof.

10. A composition for cleaning bacterial cellulose deposits comprising:
   from about 0.01 wt. % to about 2 wt. % of an enzyme composition comprising one or more of the following: a cellulase, an AA9 polypeptide having cellulolytic enhancing activity, a hemicellulase, an esterase, an expansin, a laccase, a ligninolytic enzyme, a pectinase, a peroxidase, a protease, and a swollenin;
   from about 0.01 wt. % to about 7 wt. % of a nonionic surfactant, wherein the nonionic surfactant an alcohol ethoxylate, a polyethylene glycol sorbitan ester, a polyethylene glycol ether, a polyoxyethylene ether, a poly(propylene glycol)-block-poly(ethylene glycol)-block-poly(propylene glycol), a poly(ethylene glycol)-block-poly(propylene glycol)-block-poly(ethylene glycol), or mixture thereof, and has an HLB value between 13 and 18;
   from about 0.1 wt. % to about 5 wt. % of a buffering agent; wherein the buffering agent comprises CAPS, CHES, HEPBS, HEPES, HEPPS, MOPS, MES, Tris, an organic acid or salt thereof, an inorganic acid or salt thereof, or a mixture thereof;
   from about 0.01 wt. % to about 30 wt. % of a stabilizing agent comprising glycerol, polyethylene glycol 200, polyethylene glycol 400, propylene glycol, sucrose, or a mixture thereof; and
   from about 55 wt. % to about 97 wt. % of water;
   wherein the composition has a pH of between about 3 and about 4.75.

11. The composition of claim 10, wherein the cellulase comprises a cellobiohydrolase, an endoglucanase, a beta glucosidase, or a combination or mixture thereof.

12. The composition of claim 11, wherein the cellulase is derived from an expression product of *Trichoderma reesei*.

13. The composition of claim 10, wherein the composition further comprises a colorant, an additional enzyme, a fragrance, an additional surfactant, a thickening agent, or a mixture thereof.

14. A method of cleaning a bacterial cellulose deposit comprises:
   (a) contacting a hard surface with the composition of claim 1 for a sufficient time to at least partially degrade the bacterial cellulose deposit.

15. The method of claim 14, wherein a sufficient time is at least about 5 seconds.

16. The method of claim 15, wherein method further comprises a step:
   (b) rinsing the hard surface with water at a temperature between about 10° C. and about 100° C.

* * * * *